United States Patent [19]

Kim et al.

[11] Patent Number: 5,414,166
[45] Date of Patent: May 9, 1995

[54] PROCESS FOR THE PREPARATION OF 1,1,1-TRIFLUORO-2,2-DICHLOROETHANE

[75] Inventors: Hoon S. Kim; Kun Y. Park; Byung G. Lee, all of Seoul, Rep. of Korea

[73] Assignee: Korea Institute of Science and Technology, Seoul, Rep. of Korea

[21] Appl. No.: 158,316

[22] Filed: Nov. 29, 1993

[51] Int. Cl.$^6$ ............................................. C07C 19/08
[52] U.S. Cl. ...................................... 570/176; 570/123
[58] Field of Search ................................ 570/123, 176

[56] References Cited

U.S. PATENT DOCUMENTS 4,060,469 11/1977 Sweeney et al. .
5,120,883 6/1992 Rao et al. ............................... 570/123
5,132,473 7/1992 Furutaka et al. ..................... 570/123

FOREIGN PATENT DOCUMENTS 0346612 12/1989 European Pat. Off. .

Primary Examiner—Alan Siegel
Attorney, Agent, or Firm—Oblon, Spivak, McClelland, Maier & Neustadt

[57] ABSTRACT

This specification discloses a process for the preparation of 1,1,1-trifluoro-2,2-dichloroethane in which chlorination of 1,1,1-trifluoro-2-chloroethane is carried out in the presence of activated carbon by feeding chlorine and hydrogen into a reactor simultaneously or sequentially, thereby enhancing the selectivity to 1,1,1-trifluoro-2,2-dichloroethane without lowering the conversion of 1,1,1-trifluoro-2-chloroethane.

19 Claims, No Drawings

PROCESS FOR THE PREPARATION OF 1,1,1-TRIFLUORO-2,2-DICHLOROETHANE

BACKGROUND OF THE INVENTION

1. Field of the Invention

The present invention relates to a process for the preparation of 1,1,1-trifluoro-2,2-dichloroethane ($CF_3CHCl_2$). More particularly, the present invention relates to an improved process for the preparation of 1,1,1-trifluoro-2,2-dichloroethane in which chlorination of 1,1,1-trifluoro-2-chloroethane ($CF_3CH_2Cl$) is carried out by feeding chlorine and hydrogen into a reactor simultaneously or sequentially in the presence of activated carbon, thereby enhancing the selectivity to 1,1,1-trifluoro-2,2-dichloroethane.

2. Description of the Prior Art 1,1,1-trifluoro-2,2-dichloroethane has similar physical properties to trifluorochloromethane ($CF_3Cl$, known commercially as "CFC-11"), but it hardly decomposes the ozone layer and shows little influence on the warming of the earth. For these reasons, 1,1,1-trifluoro-2,2-dichloroethane is attractive commercially as a potential substitute for CFC-11.

A number of processes for the preparation of 1,1,1-trifluoro-2,2-dichloroethane have been suggested. For example, European Patent Publication No. 0 346 612 A, and Japanese Patent Kokai (Laid-Open) Publication No. 89-290638, disclose a process for the preparation of 1,1,1-trifluoro-2,2-dichloroethane which comprises chlorinating 1,1,1-trifluoro-2-chloroethane in the presence of a catalyst such as $CuCl_2$, $NiCl_2$, and $FeCl_2$ carried on $AlF_3$. U.S. Pat. No. 4,060,469 discloses a process for the preparation of 1,1,1-trifluoro-2,2-dichloroethane which comprises photochlorinating 1,1,1-trifluoro-2-chloroethane under a radiation of specific wavelength range.

In general, a chlorination of 1,1,1-trifluoro-2-chloroethane is carried out stepwise in accordance with following reactions:

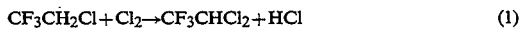

$$CF_3CH_2Cl + Cl_2 \rightarrow CF_3CHCl_2 + HCl \quad (1)$$

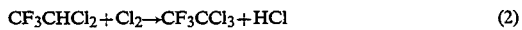

$$CF_3CHCl_2 + Cl_2 \rightarrow CF_3CCl_3 + HCl \quad (2)$$

In the above reactions, Sequence (1) is the reaction of interest, and Sequence (2) is an undesired side reaction. However, it has been reported that the rate of Sequence (2) is faster than that of Sequence (1). Due to these characteristics, an amount of unnecessary by-product, $CF_3CCl_3$, in addition to the desired chlorinated product, $CF_3CHCl_2$, has been inevitably produced in the prior art processes. The by-product, $CF_3CCl_3$ needs additional processes and apparatus for its treatment.

Attempts have been made to overcome the problems mentioned above by increasing the selectivity to $CF_3CHCl_2$ as much as possible. A typical process is disclosed in U.S. Pat. No. 4,060,469 and Japanese Patent Kokai (Laid-Open) Publication No. 91-52831, in which chlorination is carried out at a low molar ratio of $Cl_2$ to $CF_3CH_2Cl$ so as to suppress production of $CF_3CCl_3$. However, this process causes the problem that the conversion ratio of $CF_3CH_2Cl$ is low, rendering the process economically ineffective.

SUMMARY OF THE INVENTION

It is, therefore, an object of the present invention to provide an improved process for the preparation of $CF_3CHCl_2$ in which chlorination of $CF_3CH_2Cl$ is carried out with increased selectivity to $CF_3CHCl_2$.

It is another object of the present invention to provide an economically efficient process for the preparation of $CF_3CHCl_2$ in which the additional steps for treating $CF_3CCl_3$ are made unnecessary by suppressing the formation of $CF_3CCl_3$.

Further objects of the present invention will become apparent through reading the remainder of the specification.

DETAILED DESCRIPTION OF THE INVENTION

We, the inventors, have unexpectedly found that when chlorination of $CF_3CH_2Cl$ is carried out by using chlorine together with hydrogen in the presence of activated carbon, the resulting $CF_3CCl_3$ by-product can be converted into $CF_3CHCl_2$ by hydrogenation; thus, greatly enhancing the selectivity to $CF_3CHCl_2$.

The present invention provides a process for the chlorination of $CF_3CH_2Cl$. The process is characterized in that hydrogen is used for the chlorination of $CF_3CH_2Cl$ using chlorine in the presence of activated carbon. The hydrogen used reacts with the $CF_3CCl_3$ formed by the chlorination to convert it into the desired product, $CF_3CHCl_2$.

The chlorination of $CF_3CH_2Cl$ and the hydrogenation of $CF_3CCl_3$ may usually be conducted at a temperature ranging from 250° to 500° C. However, at temperatures lower than 350° C., the reaction rate is lowered, making the overall process inefficient. However, if the reaction temperature exceeds 450° C., many problems such as the risks of decomposition of the reaction products and deactivation of the catalyst may occur. For these reasons, it is preferred to carry out the reactions at the temperature ranging from 350° to 450° C.

The contact time between the reactants and the catalyst ranges from 1 to 90 seconds, and preferably, from 15 to 45 seconds. The molar ratio of chlorine to $CF_3CH_2Cl$ ranges from 0.5 to 10, and preferably, from 1 to 5. The molar ratio of hydrogen to $CF_3CH_2Cl$ ranges from 0.25 to 5, and preferably, from 0.5 to 3.

The hydrogen and chlorine gases are preferably simultaneously fed into a reaction vessel. Alternatively, chlorine and then, hydrogen may be fed into the reaction vessel.

The chlorination may be carried out under atmospheric pressure. However, it is preferable to carry out the reaction at a pressure ranging from 8 to 10 atms in order to increase the selectivity to $CF_3CHCl_2$, and to ensure efficient separation of the by-product, HCl. A higher pressure may be employed to obtain a longer contact time between the reactants and the catalyst, which increases the conversion of $CF_3CH_2Cl$ and the yield of $CF_3CHCl_2$.

Chlorination vessels are known in the art. Any known vessel made of anti-corrosive materials may be used in the present invention. The preferred vessels are those made of Inconel-600, Hastelloy-C, nickel, and the like.

According to the present invention, since the by-product, $CF_3CCl_3$, is converted into $CF_3CHCl_2$ by hydrogenation, the selectivity to $CF_3CHCl_2$ can be greatly enhanced. Due to the fact that the hydrogenation is conducted in the same reaction vessel, the process of the present invention does not impose any restrictions on the process conditions, which are the major factors to decrease the productivity in the prior art techniques, for example, to maintain the conversion ratios of $CF_3CH_2Cl$ at a low level, in order to increase the selectivity to $CF_3CHCl_2$.

DESCRIPTION OF THE PREFERRED EMBODIMENTS

The present invention will be illustrated in greater detail by way of the following examples. The examples are presented for illustration purposes only and should not be construed as limiting the invention which is properly delineated in the claims.

EXAMPLE 1

A cylindrical reaction vessel made using an Inconel-600 tube having a diameter of 2.54 cm and a length of 30 cm was used. Activated carbon, in the form of pellets of 3 mm in diameter and 5 mm in length (available from Kanto Chemical Co., Inc., Tokyo, Japan), was packed into the vessel. $CF_3CH_2Cl$, chlorine, and hydrogen were simultaneously fed into the vessel to produce $CF_3CHCl_2$. The molar ratio of the fed $CF_3CHCl_2$, chlorine, and hydrogen was maintained at 1:1:0.5. The reaction temperature was 450° C., and the reaction time was 30 seconds. The above reactants were introduced into the vessel after the vessel was preheated to 200° C. A mass flow controller was used in order to ensure a quantitative supply of the reactants. The effluent from the reactor was washed in turn with an aqueous NaOH solution and water to remove $Cl_2$ and HCl, dried with $CaCl_2$, cooled at $-20°$ C., and collected. The product was subjected to gas chromatograph using the Krytox-143AC column.

The composition ratio of the resulting product is shown in Table 1 below.

COMPARATIVE EXAMPLE 1

The same chlorination reaction as described in Example 1 was carried out by using the same reaction vessel under the same reaction conditions, except that only $CF_3CH_2Cl$ and chlorine were fed into the reaction vessel in the absence of a catalyst.

The composition ratio of the resulting product is shown in Table 1 below.

TABLE 1

| Example No. | Component | | |
|---|---|---|---|
| | $CF_3CH_2Cl$ | $CF_3CHCl_2$ | $CF_3CCl_3$ |
| Example 1 | 39.8% | 52.8% | 7.4% |
| Comparative Example 1 | 37.0% | 33.9% | 29.1% |

EXAMPLES 2–9

The same chlorination reaction as in Example 1 was carried out in the same reaction vessel, but while varying the reaction conditions. The conversion of $CF_3CH_2Cl$ and the selectivity to $CF_3CHCl_2$ are defined as follows.

$$\text{Conversion of } CF_3CH_2Cl = \frac{\left(\begin{array}{c}\text{Amounts of}\\CF_3CH_2Cl \text{ Fed}\end{array}\right) - \left(\begin{array}{c}\text{Amounts of}\\CF_3CH_2Cl \text{ Unreacted}\end{array}\right)}{\text{Amounts of } CF_3CH_2Cl \text{ Fed}} \times 100$$

$$\text{Selectivity to } CF_3CHCl_2 = \frac{\text{Amounts of } CF_3CHCl_2 \text{ Produced}}{\text{Total Amounts of Reaction Products}}$$

The results are listed in Table 2 below.

TABLE 2

| Example No. | $T^1$ | $R_a{}^2$ | $R_b{}^3$ | $T^4$ | $C^5$ | $S^6$ |
|---|---|---|---|---|---|---|
| 2 | 450 | 1.0 | 1.0 | 30 | 55.0 | 0.88 |
| 3 | 450 | 2.0 | 0.5 | 30 | 71.2 | 0.65 |
| 4 | 400 | 1.0 | 0.5 | 30 | 46.7 | 0.78 |
| 5 | 350 | 1.0 | 0.5 | 30 | 42.8 | 0.76 |
| 6 | 450 | 1.0 | 1.0 | 15 | 49.2 | 0.87 |
| 7 | 450 | 1.0 | 1.0 | 60 | 66.2 | 0.86 |
| 8 | 450 | 5.0 | 1.0 | 30 | 79.2 | 0.86 |
| 9 | 450 | 1.0 | 3.0 | 30 | 59.2 | 0.92 |

Remarks:
$T^1$ = reaction temperature (°C.)
$R_a{}^2$ = molar ratio of $Cl_2$ to $CF_3CH_2Cl$
$R_b{}^3$ = molar ratio of $H_2$ to $CF_3CH_2Cl$
$T^4$ = contact time (seconds)
$C^5$ = conversion of $CF_3CH_2Cl$ (mole %)
$S^6$ = selectivity to $CF_3CHCl_2$

What is claimed is:

1. A process for the preparation of 1,1,1-trifluoro-2,2-dichloroethane comprising chlorinating 1,1,1-trifluoro-2-chloroethane with chlorine and hydrogen in the presence of activated carbon in a reactor, said chlorine and said hydrogen being fed into said reactor simultaneously or sequentially.

2. The process of claim 1, wherein the molar ratio of said chlorine to said 1,1,1-trifluoro-2-chloroethane ranges from 0.5 to 10.

3. The process of claim 2, wherein the molar ratio of said chlorine to said 1,1,1-trifluoro-2-chloroethane ranges from 1 to 5.

4. The process of claim 1, wherein said chlorination is carried out at a temperature ranging from 250° to 500° C.

5. The process of claim 4, wherein said chlorination is carried out at a temperature ranging from 350° to 450° C.

6. The process of claim 1, wherein the reaction time for said chlorination ranges from 1 to 90 seconds.

7. The process of claim 6, wherein the reaction time for said chlorination ranges from 15 to 40 seconds.

8. The process of claim 1, wherein said chlorine is fed into said reactor simultaneously with said hydrogen.

9. The process of claim 8, wherein after first feeding said chlorine into said reactor, said hydrogen is fed into the same reactor.

10. A process for the preparation of 1,1,1-trifluoro-2,2-dichloroethane comprising chlorinating 1,1,1-trifluoro-2-chloroethane with chlorine and hydrogen in the presence of activated carbon in a reactor, said chlorine and said hydrogen being fed into said reactor simultaneously or sequentially, wherein the molar ratio of said hydrogen and said 1,1,1-trifluoro-2-chloroethane ranges from 0.25 to 5.

11. The process of claim 10, wherein the molar ratio of said hydrogen to said 1,1,1-trifluoro-2-chloroethane ranges from 0.5 to 3.

12. The process of claim 10, wherein said chlorine and said hydrogen are fed into said reactor simultaneously.

13. The process of claim 10, wherein said chlorine and said hydrogen are fed into said reactor sequentially.

14. The process of claim 10, wherein the molar ratio of said chlorine to said 1,1,1-trifluoro-2-chloroethane ranges from 0.5 to 10.

15. The process of claim 10, wherein the molar ratio of said chlorine to said 1,1,1-trifluoro-2-chloroethane ranges from 1 to 5.

16. The process of claim 10, wherein said chlorination is carried out at a temperature ranging from 250° to 500° C.

17. The process of claim 16, wherein said chlorination is carried out a temperature ranging from 350° to 450° C.

18. The process of claim 10, wherein the reaction time for said chlorination ranges from 1 to 90 seconds.

19. The process of claim 10, wherein the reaction time for said chlorination ranges from 15 to 40 seconds.

* * * * *